United States Patent [19]
Dunshee et al.

[11] Patent Number: 5,914,282
[45] Date of Patent: Jun. 22, 1999

[54] ADHESIVE SHEET ARTICLES

[75] Inventors: Wayne K. Dunshee, Maplewood; Steven C. Stickels, Woodbury, both of Minn.

[73] Assignee: Minnesota Mining and Manufacturing Company, St. Paul, Minn.

[21] Appl. No.: 08/774,450

[22] Filed: Dec. 30, 1996

Related U.S. Application Data

[63] Continuation of application No. 08/391,658, Feb. 21, 1995, abandoned.

[51] Int. Cl.⁶ .............................. A61F 13/00; B32B 7/12
[52] U.S. Cl. ........................... 442/76; 604/304; 604/307; 428/343
[58] Field of Search ..................... 428/343, 354, 428/355 R, 355 AC; 604/304, 307; 442/76

[56] References Cited

U.S. PATENT DOCUMENTS

| | | | |
|---|---|---|---|
| 3,121,021 | 2/1964 | Copeland | 117/122 |
| 3,307,545 | 3/1967 | Surowitz | 128/156 |
| 3,678,933 | 7/1972 | Moore et al. | 128/296 |
| 4,112,177 | 9/1978 | Salditt et al. | 428/304 |
| 4,552,802 | 11/1985 | Mechin | 428/255 |
| 4,561,435 | 12/1985 | McKnight et al. | 128/156 |
| 4,693,776 | 9/1987 | Krampe et al. | 156/327 |
| 4,733,659 | 3/1988 | Edenbaum et al. | 128/156 |
| 4,743,232 | 5/1988 | Kruger | 604/180 |
| 4,743,499 | 5/1988 | Volke | 428/317.3 |
| 4,773,409 | 9/1988 | Cilento et al. | 128/156 |
| 4,798,201 | 1/1989 | Rawlings et al. | 128/156 |
| 4,842,924 | 6/1989 | Farris et al. | 428/221 |
| 4,880,690 | 11/1989 | Szycher et al. | 428/224 |
| 4,900,608 | 2/1990 | Stamper | 428/151 |
| 4,901,714 | 2/1990 | Jensen | 128/156 |
| 4,957,795 | 9/1990 | Riedel | 428/74 |
| 4,957,806 | 9/1990 | Pangrazi et al. | 428/224 |
| 5,032,450 | 7/1991 | Rechlicz et al. | 428/196 |
| 5,086,764 | 2/1992 | Gilman | 602/42 |
| 5,123,900 | 6/1992 | Wick | 602/41 |

(List continued on next page.)

FOREIGN PATENT DOCUMENTS

| | | |
|---|---|---|
| 0 385 611 | 9/1990 | European Pat. Off. . |
| 385611 A2 | 9/1990 | European Pat. Off. . |
| WO 93/11728 | 6/1993 | WIPO .............. A61F 13/58 |
| WO 94/23609 | 10/1994 | WIPO .............. A44B 18/00 |

OTHER PUBLICATIONS

"ALLDRESS: Sterile Multi Layered Wound Dressing", A Brochure of The Scott Chronic Wound Care System.
"How to Use Alldress", A Brochure of Scott Paper Company; Scott Health Care Unit (1991).
"COVADERM PLUS: Adhesive Barrier Wound Dressing", Brochure of DeRoyal Wound Care.
"COVADERM PLUS: Adhesive Barrier Wound Dressing", Brochure of DeRoyal Wound Care, A Division of DeRoyal Industries, Inc., Powell, TN.
"COVADERM PLUS V.A.D. DRESSING; Adhesive Vascular Access Device Dressing", Brochure of DeRoyal Wound Care, A Division of DeRoayl Industries, Inc., Powell, TN.
Product Sample of–COVADERM PLUS: Adhesive Barrier Dressing 46–401, DeRoyal Wound Care.

*Primary Examiner*—Daniel Zirker
*Attorney, Agent, or Firm*—Stephen W. Bauer; Ann M. Mueting; Amelia A. Buharin

[57] ABSTRACT

An adhesive sheet article comprising a porous backing coated on one side with a polymeric migration barrier and said migration barrier is further coated with a pressure-sensitive adhesive to provide novel adhesive tape articles. A method of manufacturing such articles is also disclosed.

12 Claims, 5 Drawing Sheets

U.S. PATENT DOCUMENTS

| | | | |
|---|---|---|---|
| 5,153,040 | 10/1992 | Faasse, Jr. | 428/354 X |
| 5,158,555 | 10/1992 | Porzilli | 604/307 |
| 5,230,350 | 7/1993 | Fentress | 128/846 |
| 5,246,750 | 9/1993 | Dinklage et al. | 428/34.8 |
| 5,264,281 | 11/1993 | Arakawa et al. | 428/354 |
| 5,277,954 | 1/1994 | Carpenter et al. | 428/354 X |
| 5,322,695 | 6/1994 | Shah et al. | 424/448 |
| 5,326,630 | 7/1994 | Saito et al. | 428/231 |
| 5,344,415 | 9/1994 | DeBusk et al. | 604/304 |
| 5,368,920 | 11/1994 | Schortmann | 428/224 |
| 5,370,924 | 12/1994 | Kochinke | 428/224 |
| 5,455,043 | 10/1995 | Fischel-Ghodsian | 428/354 X |
| 5,648,166 | 7/1997 | Dunshee | 428/355 AC |

ADHESIVE SHEET ARTICLES

This is a continuation of Application Ser. No. 08/391,658 filed Feb. 21, 1995, abandonded.

FIELD OF THE INVENTION

The invention relates to adhesive sheet articles comprising porous sheets with a polymeric composition adhered thereto which is further coated with an adhesive. The invention further relates to adhesive articles such as tapes or wound dressings made from the adhesive sheet articles and methods for making the adhesive articles.

BACKGROUND OF THE INVENTION

Sheet materials having physical characteristics which allow for air permeability and moisture vapor permeability are well known and are generally referred to as porous sheets. Porous sheet materials are typically non-woven, woven or knitted constructions although foamed sheets, microporous films and perforated films also provide certain degrees of permeability.

Porous sheet materials have many applications and are particularly useful as backings for tapes in the medical field. This is particularly true when it is desirable to allow the skin covered by the sheet material to breathe. When an adhesive is coated onto a porous sheet, the adhesive sheet article will exhibit varying degrees of breathability depending upon the nature of both the porous sheet and the adhesive coated thereon. For example, Copeland in U.S. Pat. No. 3,121,021 describes a breathable surgical tape made of a non-woven backing and a microporous layer of pressure-sensitive adhesive.

Certain porous sheets coated with adhesive may permit or even facilitate the migration of adhesives into the porous sheet layer. Such migration of adhesives is not always detrimental to the performance of the adhesive tape article. This is true if a heavy adhesive coating is used or if the adhesive is used for transdermal delivery of a bioactive molecule. However, it is sometimes detrimental when the adhesive migrates into the porous sheets. This is true when adhesion of the resulting article is reduced due to the migrated adhesive.

When it is necessary to control or limit the migration of adhesive, a few strategies are available. Generally, one should avoid "soft" adhesives which readily migrate into the interstices of porous backings. "Soft" adhesives include adhesives such as acrylate ester-acrylic acid-polyethylene oxide acrylate macromer copolymers which provide adhesive coated sheet materials having a skin adhesion value of at least about 2.2 Newtons per 100 millimeters of width. However, such "soft" adhesives are very desirable for adhering to skin because "soft" adhesives are generally very conformable and usually adhere well to skin, and may adhere to moist skin.

U.S. Pat. No. 5,344,415 of DeBusk and Felice (hereinafter "DeBusk") describes a multi-component system which includes a web and adhesive layer, a barrier layer and a second adhesive layer. The DeBusk barrier layer is a distinct and separate transparent nonexclusive film material such as a polyurethane film. As is generally known in the art, films must be at least 25 micrometers thick in order to allow handling of the film. The DeBusk barrier layer (film) is sandwiched between 2 layers of adhesive and does not directly contact the web. DeBusk teaches that the barrier layer provides a barrier to external contaminants, restricts drainage strike-through and helps maintain a desirable moist environment.

It is an object of the present invention to provide porous adhesive sheet articles wherein the migration of the soft adhesives into the porous sheeting is limited or prevented.

SUMMARY OF THE INVENTION

Figure 1:
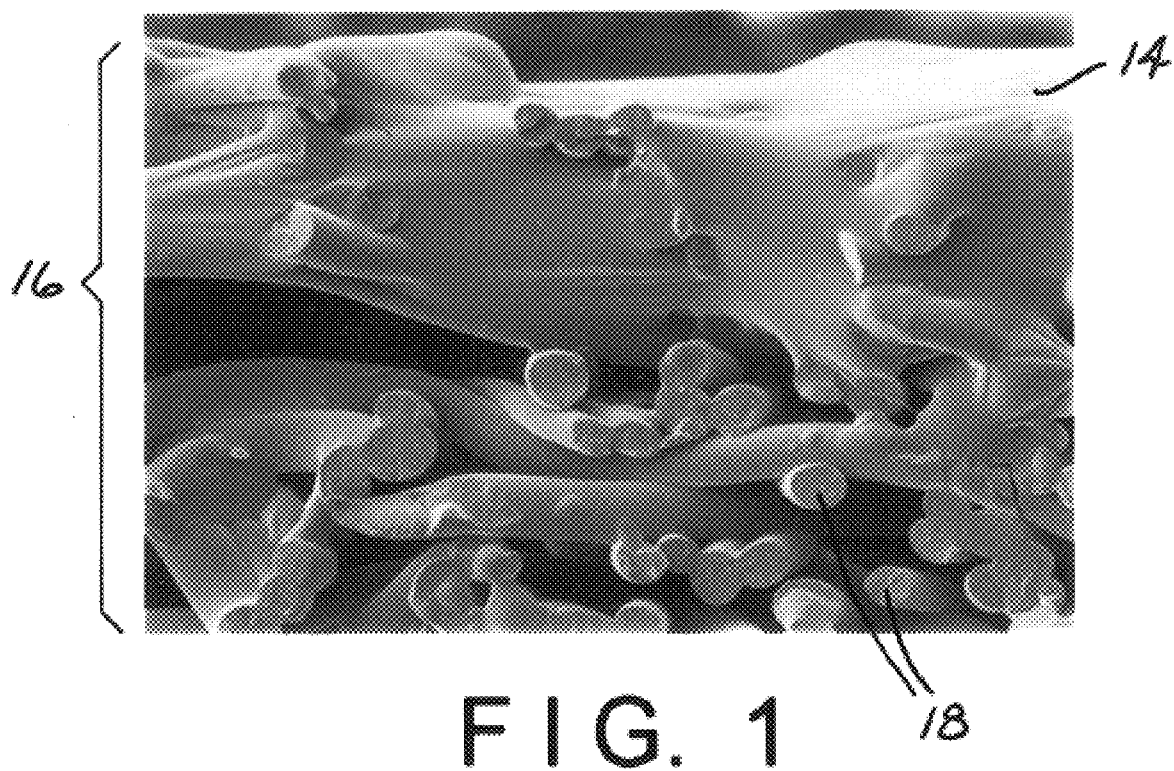
FIG. 1 is a 500 times magnification scanning electron micrograph (SEM) of a nonwoven web coated with an adhesive.

The present invention provides adhesive sheet articles. More specifically, it provides adhesive sheet articles comprising porous backings with a polymeric composition juxtaposed between said backing and the adhesive layer to prevent migration of the adhesive into the porous backing.

This invention further provides such adhesive sheet articles which are converted to provide pressure-sensitive adhesive tape articles or first aid dressings. Although sheet articles comprising porous backings adhered to non-tacky polymeric migration barriers and further adhered to skin adhesives are a preferred sub-class, sheet articles comprised of porous backings with any non-film barrier layer which adheres to both the backing and the adhesive are broadly described. This invention further relates to nontacky or tacky migration barrier layers which are polymeric coatings of acrylate copolymers or polyurethanes juxtaposed between an adhesive and a porous backing. Preferred polymeric coatings are acrylate copolymers.

This invention also provides a process for preparing a pressure-sensitive adhesive tape article comprising depositing a polymeric migration barrier coating on one side of a pressure-sensitive adhesive layer, then adhering the exposed side of the polymeric migration barrier coating to a porous backing.

Definitions

As used herein the term "coating" refers to an essentially continuous macroscopically nonporous chemically homogeneous layer which has been deposited on or bonded to or adhered to a separately nonsimultaneously formed, deposited or otherwise provided layer.

As described herein the term "breathable" refers to materials which are penetrable by air and water vapor preferably to the extent that they provide a moisture vapor transmission rate (MVTR) of at least 200 g/m$^2$ per 24 hours when measured in accordance with ASTM E 96-80 or minor modifications thereof.

As used herein the term "porous" refers to materials or surfaces which are penetrable by smaller objects or materials. Such porous materials or surfaces do not necessarily have visible openings, although they may, but have visible characteristics consistent with permeability and penetration. Some examples of porous materials are nonwoven polymeric webs, woven cloth or polymeric fabrics, knitted cloth or nonwoven fabrics, absorbent spongelike foams and the like but do not include films or other nonbreathable layers.

DETAILED DESCRIPTION OF THE INVENTION

The adhesive sheet articles of the invention comprise a porous backing, a migration barrier layer comprised of a polymeric composition coated on the backing with an adhesive layer coated on the barrier layer. The migration barrier is preferably less than 20 µm thick. Preferred articles of the invention comprise an adhesive sheet article with moisture vapor transmission rates of at least 400 g/m$^2$ per 24 hours. The adhesives are first described, followed by a discussion of the porous backings and a discussion of the polymeric migration barrier.

Adhesive

As stated earlier, the adhesives which are preferred for contact with human skin are "soft" adhesives. Such soft adhesives would readily migrate into a porous backing. Nonlimiting examples of soft adhesives include hydrophilic adhesives or blends including hydrophilic adhesive components.

Examples of suitable soft hydrophilic adhesives for use on the articles of the invention include pressure sensitive adhesives which are water insoluble and not significantly water absorbent and water tolerant such as polyacrylates, polyolefins e.g. polyalpha-olefins, polyethers, polyisoprenes, butyl rubbers, natural rubbers, styrene-butadiene rubbers, polyurethanes, polyesters and the like. It is anticipated that blends or mixtures of such adhesives are useful in the present invention and the adhesives may optionally include tackifiers. Preferred adhesives are acrylate ester-acrylic acid-polyether macromer copolymers described below as second polymeric components and polymer blends thereof. The blends are novel materials described in copending application F.N. 51439USA4A incorporated herein by reference.

Such adhesive blends comprise primarily two components. The components are each described in detail below followed by a description of the method of blending the two components.

First Polymeric Component of a Preferred Adhesive Blend

The first polymeric component increases the initial adhesion of the adhesive blend to the skin while retaining the typical advantages of acrylate ester adhesives when used as medical adhesives. This component is comprised of certain copolymers which are used as skin adhesives for medical applications and are described in U.S. Pat. No. 4,693,776 of Krampe, Moore and Taylor (Krampe) entitled "Macromer Reinforced Pressure Sensitive Skin Adhesive" which is hereby entirely incorporated by reference. The typical advantages of these adhesives include ease of manufacture, an excellent safety history and profile, high shear strength, low cost and chemical stability. This first polymeric component comprises certain copolymers, especially the A-B-C type copolymers of (A) acrylate esters, (B) ethylenically unsaturated compounds copolymerizable with acrylate esters such as acrylic and methacrylic acid and (C) macromolecular monomers as described hereinafter. The acrylic esters may be esters of acrylic or methacrylic acid and are preferably acrylic acid esters. The alcohol portion of the ester is typically a non-tertiary alcohol having one to fourteen carbon atoms with the average number of carbon atoms being about four to twelve. In a preferred embodiment the average number of carbon atoms is about six to ten, and most preferably about eight. Nonlimiting examples include isooctyl acrylate and ethyl(hexyl) acrylate.

The ethylenically unsaturated compounds (B monomers) copolymerizable with acrylate (and methacrylate) esters include acrylic acid, methacrylic acid, itaconic acid, acrylamide, methacrylamide, acrylonitrile, methacrylonitrile, vinyl acetate and N-vinylpyrrolidone, but acrylic acid is used in a preferred embodiment.

The macromolecular monomers (macromers) useful as C monomers have the general formula: X-(Y)$_n$-Z wherein X is a vinyl group copolymerizable with said A and B monomers; Y is a divalent linking group; where $n$ can be zero or 1; and Z is a monovalent polymeric moiety having a T$_g$ greater than about 20° C. and a molecular weight in the range of about 2,000 to about 30,000 and being essentially unreactive under copolymerization conditions; wherein said vinyl group and said A and B monomers form a polymeric backbone having pendant therefrom said polymeric moieties (Z) and wherein the molecular weight of said C macromer and the inherent viscosity of the copolymer are such that the adhesive composition has a creep compliance value of at least about 1.2×10$^{-5}$cm$^2$/dyne. In a preferred embodiment C macromers are polystyrylethyl methacrylate macromers having a weight average molecular weight of about 8,000 to 15,000 g/mol. and most preferably about 10,000 g/mol. as described in Example M-3 of U.S. Pat. No. 4,693,776 and hereinafter in Example 1. These macromers are prepared by reaction of styrene with secondary-butyl lithium in cyclohexane to form "living polymers" of polystyryl lithium, "capping" with ethylene oxide, followed by reaction with methacryloyl chloride to obtain a macromer of about 10,000 weight average molecular weight. Some macromers useful in the present invention are commercially available, e.g. polystyrylethyl methacrylate (13,000M. wt.) is available as Chemlink® 4500 from Sartomer Chemical Company of West Chester, Pa.

The amounts of A, B and C monomers in these copolymers are typically 90 percent or more by weight of A monomer and about equal amounts of B and C monomers. A nonlimiting example of the amounts of monomer in the copolymer is 96 parts A monomer, 2 parts of B monomer and 2 parts of C monomer.

Second Polymeric Component of a Preferred Adhesive Blend

The second main component of the polymer blends useful in the present invention promotes prolonged adhesion to skin, which is a relatively moist substrate. Medical tapes which adhere well to moist skin generally require adhesives which are substantially hydrophilic and polar in character. One such class of adhesives is described in PCT Application WO 84/03837 of Snyder and Spence (Snyder) entitled "Adhesive and Adhesive-Coated Sheet Material for Moist Skin" which is hereby entirely incorporated by reference.

These second copolymers include three comonomers. A first comonomer is an acrylic acid ester of a non-tertiary alcohol, said alcohol having from about 4 to 14 carbon atoms. In a preferred embodiment the alcohol has about 8 carbon atoms. Examples include but are not limited to isooctyl or ethylhexyl alcohol. In a preferred embodiment the alcohol is isooctyl alcohol.

The second copolymer includes a second comonomer which is a hydrophilic monomer having a vinyl group copolymerizable with the acrylate ester monomer, a divalent linking group and a monovalent polyether group. The polyether group should be essentially unreactive under conditions used for forming the copolymer. Many such second comonomers are described in Snyder. These comonomers contain a plurality of hydrophilic sites such as ether groups. Preferred second comonomers are macromolecular monomers of the formula:

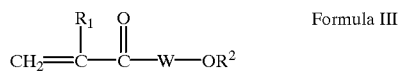

Formula III wherein $R_1$ is hydrogen or methyl, $R^2$ is hydrogen, phenyl, substituted phenyl or lower alkyl and W is a divalent poly(lower alkylene oxide) group containing 2 to 250 repeating alkoxy units and selected from the group consisting of a poly(ethylene oxide) radical, a poly(propylene oxide) radical, a radical of a copolymer of ethylene oxide and propylene oxide and a polytetrahydrofuran radical.

In a preferred embodiment the W moiety contains about 5 to 25 repeating alkoxy units, most preferably ethylenoxy units, and $R^2$ is hydrogen or lower alkyl. Such second monomers are commonly commercially available as alkoxypoly(ethylenoxy)alcohols such as methoxypoly(ethylenoxy)ethanols of various molecular weights. Synthesis and description of various additional suitable materials as found in Snyder is as follows:

A variety of second monomers are or have been available commercially. For example, suitable commercially available monomers are the 2-(2-ethoxyethoxy)ethyl acrylate available under the trade designation "SR-256" from Sartomer Company, West Chester, Pa.; the methoxy poly(ethylene oxide)$_{10}$ acrylate available under the trade designation "No. 8816" from Monomer-Polymer & Dajac Laboratories, Inc., Trevose, Pa.; the methoxy poly(ethylene oxide) methacrylates of 200 Daltons, 400 Daltons, and 1000 Daltons available under the trade designations "No. 16664", "No. 16665" and "No. 16666", respectively, from Polysciences, Inc., Warrington, Pa.; the hydroxy poly(ethylene oxide)$_5$ methacrylate available under the trade designation "No. 16712" from Polysciences, Inc., Warrington, Pa.

Other preferred second monomers may be prepared using commercially available starting materials and conventional methods. For example, the preferred second monomers wherein $R^2$ of Formula III is lower alkyl may be prepared by reacting an a,b-unsaturated carboxylic acid such as acrylic acid or methacrylic acid with an equimolar amount of a mono-alcohol of a poly(lower alkylene oxide). The esterification reaction is generally conducted under anhydrous conditions in an organic solvent such as toluene which preferably will form an azeotropic mixture with the water which is generated as the esterification reaction proceeds. A suitable solvent is toluene. Typically, the alcohol is combined with the organic solvent and the unsaturated carboxylic acid is then added to the alcohol/solvent mixture. In the event that the alcohol is a solid at room temperature, it is first melted by heating prior to addition of the unsaturated carboxylic acid. The reaction is conducted in the presence of an acid catalyst such as para-toluenesulfonic acid and a free-radical inhibitor such as copper powder. The reaction mixture is refluxed, generally for 16 to 18 hours under a nitrogen atmosphere, and the water generated is removed by azeotrophic distillation, for example, using a Dean Stark trap.

Examples of suitable mono-hydroxyl-terminated poly (lower alkylene oxides) which may be used to prepare the preferred second monomers using the above-described procedure include Carbowax® 350, Carbowax® 550, Carbowax® 750, Carbowax® 2000 and Carbowax® 5000 (i.e., the methoxypoly(ethylene oxide) ethanols of about 350 MW, 550 MW, 750 MW, 2000 MW and 5000 MW, respectively, commercially available from Union Carbide Corp). The Carbowax® family of monomers are methoxy(polyethylene oxide)ethanols possessing an average molecular weight expressed by the numeral e.g. the 5000 of Carbowax® 5000 denotes an average molecular weight of 5000. A monoalcohol of a polytetrahydrofuran of about 16,000 MW prepared as described in Snyder by polymerization of tetrahydrofuran in the presence of methyl trifluoromethanesulfonate as shown in Examples for Monomer "B-9" in WO 84/03837 cited above; UCON® LB-285 (an n-butoxy poly(propylene oxide) propanol having about a 1000 MW, commercially available from Union Carbide Corp.); UCON® 50-HB260 (an n-butoxy poly(ethylene oxide/propylene oxide) (50:50 by weight) alcohol having about a 1000 MW, available from Union Carbide Corp.); and Pycal® 94 (a phenoxy poly (ethylene oxide)$_4$ ethanol, available from Atlas Chemical Industries).

Second monomers wherein $R^2$ is hydrogen may be prepared by reacting an a,b-unsaturated carboxylic acid or hydroxyalkyl ester with an anhydride selected from monoepoxides, lactones or mixtures thereof.

A suitable commercially available poly(alkylene oxide) acrylate ester is NK-Ester AM 90G® available from Shin-Nakamura.

The preferred second monomer for employment in preparing the pressure-sensitive adhesive copolymer is the acrylate ester of above-described Carbowax® 750.

It is to be understood that the pressure-sensitive adhesive copolymer may comprise a single type of second monomer or may comprise two or more different second monomers.

The third monomeric component of the second copolymer is generally acrylic acid or methacrylic acid, preferably acrylic acid monomer.

Preparation of the First and Second Polymeric Components of a Preferred Adhesive Blend Either of the pressure-sensitive adhesive copolymer components of the adhesive blends useful in the invention may be prepared using conventional free-radical-polymerization methods. One particularly convenient method is the following. The desired amounts of each of the different monomers and an organic solvent in which the monomers are soluble are combined in a sealable bottle. A particularly suitable solvent is ethyl acetate. A solvent such as isopropyl alcohol which functions as a chain-transfer agent is also present in the reaction medium in order to control the molecular weight of the resulting adhesive copolymer. A catalytic amount of a free-radical initiator such as a,a'-azobisisobutyronitrile is then added to the solution. Nitrogen is bubbled through the solution to purge air from within the bottle, and the bottle is then sealed. The sealed bottle is tumbled in a heated water bath for a period of time sufficient to effect essentially complete polymerization. Generally, 24 hours has been found to be sufficient time to effect essentially complete polymerization when the water bath is maintained at about 55° C.

The hydrophilic adhesives used as the second main component of the polymer blends described above are also useful as the sole adhesive on the tape articles of the present invention.

Preparation of an Adhesive Blend Useful for the Invention

The process of blending the two copolymer components of the preferred blend adhesive of the present invention to provide a useful homogeneous pressure-sensitive adhesive requires that each of the copolymer components is dissolved in a solvent or solvent mixture. The solvents used for each of the copolymer components are preferably at least partially miscible in order to obtain good blending. Suitable solvents include esters such as ethyl acetate, dimethyl sulfoxide and N,N-dimethylformamide. Cyclohexane may be used to allow dispersions in solvent. Blending is observed visually to determine that incompatible phases are not present. It may be useful to heat one or more of the solvent mixtures to improve blending. Once mixing of the solutions of the copolymers has provided a homogeneous blend, it is preferred to coat the adhesives onto a substrate as soon as practical, but in all cases before any significant non-homogeneity of the blend is observed. Non-homogeneity would be observed e.g. by formation of heterogeneous regions (known as heterogeneous "domains"). In a preferred embodiment this coating is accomplished in one to three hours. Once the adhesive blends are coated onto substrates e.g. backings and any remaining solvent is removed, the coatings of pressure-sensitive adhesive blend have been observed to remain stable and functional for extended periods. Preferred blends contain ratios of about 90:10 to 10:90 of the two components, but preferably 40 to 80 parts of the hydrophilic component.

The pressure-sensitive adhesive copolymer blends or the one component adhesives e.g. hydrophilic adhesives of the invention may be applied to a carrier release liner by conventional methods. As is known to those skilled in the art, the particular method selected may depend upon the nature of the liner being employed. A suitable method for applying the adhesive involves coating a solution of the adhesive in water or an organic solvent or a solvent blend onto a release liner e.g. a silicone coated or fluorochemical coated liner.

It is possible to crosslink the adhesives with gamma radiation by means of the normal sterilization dose. This may be done with or without added cross-linking agents. It is preferably done without added cross-linking agents. The doses of gamma radiation used are generally 5 to 60 kilograys total dose, preferably 20 to 40 kilograys.

Porous Backings

Suitable porous backings for use in the invention are any backings which find use in medical or surgical fields. In particular the porous backings are those which are susceptible to adhesives migrating into the backing. Such backings include any of the conventional nonwoven fabrics, woven fabrics, knits, foams and the like, particularly those which permit transpiration of perspiration or wound exudate therethrough. Suitable woven, knit and nonwoven fabrics include those formed from fibers or threads of synthetic or natural materials including cotton, rayon, nylon, polyester, polyurethane and the like. Nonwoven polyurethane backings are used in a preferred embodiment. Other backings may be laminated onto selected barrier layers and adhered thereto by conventional methods such as heating, irradiation and pressure.

Nonwoven polyurethane backings which are particularly useful in the present invention can be melt blown into a separate web or directly onto a substrate for which it will serve as a backing. The polyurethane can be melt blown using a process similar to the process reported in Wente, Van A., "Superfine Thermoplastic Fibers" in *Industrial Engineering Chemistry*, Vol. 48, pages 1342 et seq (1965), or in Report No. 4364 of the Naval Research Laboratories, published May 25, 1954 titled "Manufacture of Superfine Organic Fibers" by Wente, Van A., Boone, C. D. and Fluharty, E. L. The process is exemplified hereinafter (Example 9) but is known to those skilled in the art. Typical polyurethanes useful in the process are commercially available e.g. Morthanes®, available from Morton International Inc. and Pellthanes®, available from Dow Chemical.

The backing may be of any desired shape to provide adhesive coated sheet materials embodied as adhesive tapes, strips, wound dressings, monitoring or neuro-stimulating electrodes, drapes or the like. These tapes are converted by conventional methods.

Polymeric Migration Barriers

Suitable migration barriers used in articles of the present invention are coatings of polymers which will adhere to both the porous backings and any adhesives used. Therefore, the invention does not require the additional adhesive layer required in Debusk to adhere the migration barrier to the porous backing. When coated on porous backings the migration barrier does not readily migrate into the interstices of the backing but instead adheres substantially to the surface of the backing. An adhesive coated on the migration barrier is therefore prevented from contacting the porous backing and is also prevented from migrating into the interstices of the backing. The migration barrier provides a continuous surface to which the adhesives adheres. Without being bound by theory it is believed that the migration barrier maintains a substantially continuous and smooth surface of the adhesive thus increasing the likelihood that the adhesive will adhere to any surface, particularly a rough surface such as human skin.

The migration barrier of the invention is either non-adhesive or adhesive under ambient conditions. Suitable non-adhesive coatings are polymeric coatings such as lower alkyl acrylate copolymers or polyurethanes which are not pressure-sensitive at room temperature, although these may be adhesive at higher temperatures. Such non-adhesive migration barriers are in some ways easier to process during manufacturing because they are not sticky. A preferred non-adhesive migration barrier is an ethyl acrylate N/tertiary butyl acrylamide copolymer. In order to adhere such non-adhesive migration barriers to a backing, the non-adhesive migration barriers are heated to a temperature above their softening point where the migration barrier is sufficiently tacky to allow adherence to the backing, then cooled to provide a secure bond.

Migration barriers are generally selected which will adhere to an adhesive coated thereon, i.e. an adhesive with enough chemical similarity to the migration barrier to facilitate adherence. Many suitable combinations are possible, and one skilled in the art is familiar with such suitable combinations.

When polyurethane non-wovens are used as the porous backings, it has been found that migration barriers selected from polyurethane and lower alkyl acrylate-N-lower alkylacrylamide copolymers and the like are suitable. Preferred migration barriers for polyurethane non-woven backings made from Dow Chemical Co. Pellthane® polymers or Morton International Inc. Morthane® polymers include lower alkyl acrylate-N-lower alkylacrylamide copolymers e.g. a copolymer of ethyl acrylate and tertiary butylacrylamide.

The copolymers of lower alkyl acrylates and acrylamides such as N-lower alkylacrylamides which are useful in the present invention are readily prepared using conventional free radical catalyzed processes such as those taught in Ulrich, Re 24,906 and illustrated in Example 6 hereafter.

Typically, the thickness of a migration barrier is relatively thin, e.g. 1 to 2 grains per 4 by 6 inch (4 to 8 g/m$^2$), which provides a coating thickness of about 6 to 8 microns. The migration barrier, as analyzed by scanning electron microscopy, is found to be essentially continuous.

Absorbent Pads for use in First Aid Dressings

The first aid dressings of the present invention will generally have an absorbent pad adhered thereto, either over a portion of the adhesive or in place of a portion of the adhesive and adjacent to the migration barrier as the pads are conventionally provided.

A preferred absorbent layer is a foam, woven or nonwoven material including but not limited to rayon, polyester, polyurethane, polyolefin, cellulose, cellulose derivatives, cotton, orlon, nylon, or hydrogel polymeric materials. Most preferred are woven and nonwoven materials. See, e.g., U.S. Pat. No. 4,773,903 to Weisman et al. An alternative absorbent layer includes a composite material comprising a nonwoven polymeric matrix and a highly hydrophilic fluid absorbing material. Another preferred composite material is a nonwoven matrix combined with a highly hydrophilic fluid absorbing material such as a polymeric absorbent fiber or particle selected from the group consisting of modified starches and high molecular weight acrylic polymers containing hydrophilic groups such as acrylonitrile fibers treated with alkali metal hydroxides. Suitable absorbent materials will preferably absorb at least about 25% by weight of fluid or exudate, and more preferably greater than about 100% by weight, when measured using test methods reported in U.S. Pat. No. 4,957,795 to Riedel. Another preferred class of pads is conventional non-stick pads used on first aid dressings. Nonwoven rayon web laminated to a porous high density polyethylene web such as to the 3.2 ounce single side laminate of P530 high density polyethylene mesh available from Applied Extrusion Technologies, Inc., Middletown, Del. is a preferred absorbent layer.

Suitable absorbent materials include composite materials such as nonwoven polymeric matrices combined with highly hydrophilic fluid absorbing materials. Highly hydrophilic fluid absorbing materials include polymeric absorbent fibers or particles selected from the group consisting of modified polysaccharides, modified polyurethanes, and high molecular weight acrylic polymers containing hydrophilic groups. A preferred highly hydrophilic fluid absorbing material is acrylonitrile fibers treated with alkali metal hydroxides. A commercially available hydrogel polymeric material is available under the tradename LANSEAL fiber (Japan Exlan Co., Ltd., Osaka, Japan). These types of composite absorbent materials are readily prepared using well known methods such as the method reported in U.S. Pat. No. 4,957,795 to Riedel.

A variety of means are suitable for attaching or fixing the elastic substrate to the absorbent layer such as stitching, needle-tacking, ultrasonic welding or bonding with a suitable adhesive. A preferred adhesive is a biocompatible adhesive that is selected from the group consisting of natural rubber based adhesives and acrylic based adhesives.

The following test methods were employed to evaluate the properties of articles and compositions of the invention. The present invention provides adhesive sheet articles which have desirable moisture vapor transmission rates and also maintain desirable adhesivity because the adhesives of the invention do not disappear by migrating into the porous backings of the invention. Additionally, the adhesive sheet articles of the invention are able to maintain soft textures and good conformability ratings because the migration barriers of the invention are not unduly thick or stiff.

Moisture Vapor Transmission Rate (Upright)

The Moisture Vapor Transmission Rate ($MVTR_{up}$) for the composite samples is measured in accordance with ASTM E 96-80 as modified below.

The adhesive sheet article samples are sandwiched between the adhesive surfaces of two axially aligned foil adhesive rings having 2.54 cm diameter holes. Each sample is assembled to ensure a flat, wrinkle-free and void-free foil/sample/foil laminate.

A four-ounce (0.14 kg) glass jar is filled half-full with distilled water. The jar is fitted with a screw-on cap having a 3.8 cm diameter hole concentrically aligned with a rubber washer having a 4.445 cm outside-diameter and a 2.84 cm inside-diameter.

The foil/sample/foil laminate is concentrically positioned on the rubber washer and the sample-containing subassembly screwed loosely onto the jar.

The assembly is placed into a chamber maintained at a temperature of 40° C. and 20% relative humidity. The assembly is removed from the chamber after four hours, weighed to the nearest 0.01 gram ($W_1$), and immediately returned to the chamber. The cap is now screwed tightly onto the jar without bulging of the sample. The assembly is again removed from the chamber after an additional eighteen hours and weighed to the nearest 0.01 gram ($W_2$).

The $MVTR_{up}T_{24}$ of the adhesive (measured in grams of water transmitted per square meter of sample area over a twenty four hour period) may then be calculated according the formula set forth below:

$$MVTR_{up}T_{24}=(W_1-W_2)(4.74\times10^4)/t$$

where:

($W_1$) is the initial weight of the assembly (grams)

($W_2$) is the final weight of the assembly (grams), and (t) is the time period between $W_1$ and $W_2$ (hrs).

Three samples of each adhesive were run and the average of the three samples reported.

The following examples are provided to illustrate specific embodiments of the invention, but are not intended to be limiting thereof.

Examples 1 and 3 illustrate the preparation of monomers not conveniently available from commercial sources which are necessary to make copolymers of the First and Second Polymeric Components of a preferred adhesive described hereinabove.

Examples 2, 4 and 5 describe preparation of adhesives suitable for use in the present invention.

Examples 2, 6 and 12 describe preparation of migration barriers suitable for use in the present invention.

Examples 8–19 describe preparation of samples. Table 1 provides a key which outlines construction of the samples prepared in Examples 8–19.

EXAMPLE 1

Preparation of a Polystyrylethyl Methacrylate Macromonomer

PREPARATION OF MACROMER

The "C" moiety of the general formula A-B-C is a polymeric material which has a copolymerizable vinyl group which copolymerizes with monomers A and B under polymerizing conditions. The C moiety, while being polymeric in one sense, actually behaves as a monomer and is referred to in the literature as a macromolecular monomer which is shortened to the term "macromer" for convenience. For the purposes of this invention, a representative preparation of the macromers that are used follows.

Example M-1

This methacrylate-terminated styrene macromer having an average molecular weight of about 9000 was prepared using a five-liter four-necked flask, fitted with a thermometer, mechanical stirrer, septum, Dean-Stark trap and condenser. 150 grams (1.44 moles) of styrene were charged into the flask which contained 1155 grams of cyclohexane, resulting in an 11.5% by weight solution. The solution was heated to about 50° C. and a 1.4 molar solution of secondary-butyl lithium in cyclohexane was added dropwise until a faint yellow color persisted, then 10.7 ml of additional sec-butyl lithium cyclohexane solution was added rapidly. The reaction mixture was maintained at 65° C. by cooling. After about one hour, the solution was allowed to cool to 35° C. and then ethylene oxide gas was introduced over the reaction mixture which was agitated rapidly for 15 minutes until the orange color of polystyryl lithium had disappeared. The reaction was then quenched with 5 ml (51.2 meq.) of methacryloyl chloride. The polymer solution was reduced in volume and the polymer gradually precipitated and was separated and dried. Gel permeation chromatography revealed a number average molecular weight of 8394, weight average molecular weight of 8842 and polydispersity of 1.05.

In addition to the above macromer the following macromers are prepared by the process described in Example M-1 above but gradually decreasing the amount of secondary-butyl lithium initiator to obtain higher moledular weight macromer. The macromer's molecular weight is higher if less initiator is used, as is known to the art. See e.g. U.S. Pat. No. 4,693,776 incorporated herein by reference.

Example M-2: a methacrylate-terminated polystyrene macromer having a weight average molecular weight of about 10,000 g/mol.

Example M-3: a methacrylate-terminated polystyrene macromer having a weight average molecular weight of about 13,000 g/mol.

Example M-4: a methacrylate-terminated poly(methyl methacrylate) macromer having a weight average molecular weight of about 13,000 g/mol.

Example M-5: an acrylate-terminated polymethyl methacrylate polymeric monomer having an average molecular weight of 10,000 was prepared. Recrystallized dried fluorene, five parts, was placed in a 1,000 ml three-necked flask fitted with stirrer, thermometer, argon inlet and rubber septum, all of which were previously flamed under argon. Dried tetrahydrofuran, 400 parts, was distilled into the flask and 15 parts of a 1.4N solution of sec-butyllithium in cyclohexane were added through the septum, producing an orange-red solution of "fluorenyl lithium" under slight argon pressure. The flask contents were cooled to −76° C. and 65 parts of dried, freshly distilled methyl methacrylate (MMA) were rapidly added through the septum. The reaction temperature quickly rose to −20° C. and then was gradually returned to −76° C. by cooling. After one hour of stirring, 3 parts of ethylene oxide were bubbled into the flask and the flask was warmed to −10° C., causing the liquid to change from orange-red to light yellow. Acryloyl chloride (3 parts) was then added to quench the reaction. The reaction mixture was then warmed to room temperature and added dropwise with vigorous stirring to 4 liters of hexane, causing a white solid to precipitate. The solid was filtered, dried, redissolved in toluene, filtered to remove impurities and precipitated in methanol. The resulting white solid was a polymeric monomer having the following properties: weight average molecular weight 10,420 and polydispersity 2.6.

EXAMPLE 2

Preparation of Macromer Reinforced Pressure Sensitive Adhesive Copolymer ("MRP Adhesive")

The copolymerization reaction was carried out in a sealed, one quart bottle. The one quart (0.95 liter) glass bottle was charged with 190 grams of isooctyl acrylate, 4 grams of acrylic acid, 4 grams of 2-polystyrylethyl methacrylate macromonomer prepared according to Example 1 plus 300 grams of ethyl acetate, 0.6 grams of 2,2'-azobisisobutyronitrile (available from DuPont of Wilmington, Del. as Vazo® 64), and 2.5 grams of a 1% solution of carbon tetrabromide in isooctyl acrylate that results in a 0.012% by weight charge of carbon tetrabromide. The mixture was deoxygenated by purging with nitrogen at a rate of one liter per minute for two minutes. The bottle was sealed and placed in a rotating water bath for twenty-four hours at 55° C. to effect essentially complete polymerization. The resulting copolymer was separated by partial evaporation of the solvent, filtration and drying, then resuspended and dissolved in ethyl acetate and was used in Example 5 to form an adhesive blend useful for the present invention. The copolymer can also be used as a Migration Barrier in the present invention.

EXAMPLE 3

Preparation of an Acrylate Ester of a Polyether

An acrylate ester of a polyether containing an average of about 16 repeating ethoxy units was prepared as follows.

Two hundred eighty-eight g (0.4 m) of Carbowax® 750 (a methoxy poly(ethylene oxide) ethanol of approximately 750 MW, available from Union Carbide Corp.) was melted in a 1000 ml round bottom flask fitted with a magnetic stirrer and a Dean Stark trap. Toluene, 288 g, was added to the flask and the solution was refluxed, with stirring and under a nitrogen stream, for 2 hours to remove dissolved oxygen. To this solution was then added 33.8 g (0.5 m) of acrylic acid, 9.2 g of p-toluenesulfonic acid, and 0.16 g of copper powder. The resulting mixture was then refluxed, with stirring and under a nitrogen stream, for 16 hours with generated water collected in the Dean Stark trap. The mixture was cooled to room temperature and 10 g of calcium hydroxide was added thereto. The mixture was stirred for 2 hours and then filtered through an inorganic filter aid. This polyether acrylate ester monomer was then used to prepare copolymers as described in the examples below.

EXAMPLE 4

Preparation of a Hydrophilic Adhesive

The copolymerization reaction is carried out in a sealed, four ounce bottle. The bottle is charged with 21.0 grams of isooctyl acrylate, 9.54 grams of an acrylate ester of methoxy poly(ethylene oxide) ethanol of approximately 750 molecular weight in toluene at 47.16% solids prepared according to Example 2, 4.5 grams of acrylic acid, 0.06 grams of 2,2'-azobisisobutyronitile (available from DuPont as Vazo® 64), 5.7 grams of isopropanol, and 19.26 grams of ethyl acetate. The mixture is deoxygenated by purging with nitrogen at a rate of one liter per minute for thirty-five seconds. The bottle is sealed and placed in a rotating water bath for twenty-four hours at 55° C. to effect essentially complete polymerization. The resulting copolymer product was isolated using the method described in Example 2. The copolymer product was combined with the adhesive of Example 2 and was used in Example 5 to form an adhesive blend useful for the present invention.

EXAMPLE 5

Preparation of an Adhesive Blend

A mixture of 887.5 g (32% of weight of solids) of the MRP Adhesive of Example 2 (43% solids in ethyl acetate)

and 1612.5 g (68% by weight of solids) of the Hydrophilic Adhesive of Example 4 (50% solids in ethyl acetate) was blended in a roller mill blender under ambient conditions for 96 hours to provide a solvent blend which was homogeneous to visual inspection.

EXAMPLE 6

Preparation of N-Tertiary Butvl Acrylamide-Ethyl Acrylate Copolymer Migration Barrier A pre-mix of 680.4 kg of deionized water and 177 kg of N-tertiary butyl acrylamide was prepared by mixing at high speed until the mixture was uniform. The pre-mix was charged to a 1892 liter, glass-lined reactor and agitation was set at 60 rpm. To the charged, rotating reactor was added 411.9 kg of ethyl acrylate, 371.9 kg of deionized water, 42.5 kg of Triton® X-200 (available from Union Carbide, Danbury, Conn.), and 294 grams of carbon tetrabromide. The reaction mixture was heated to 50° C., and deoxygenated using inert gas. When the temperature stabilized at 50° C., 294 grams of potassium persulfate dissolved in 2.72 kg of deionized water were charged to the reactor. The reaction was allowed to generate heat exothermically, after which the temperature was increased to 85° C. and the batch was held for thirty minutes at 85° C. The batch was then cooled to 38° C. and diluted with deionized water to 33% solids. The weight of solids present per unit volume was determined by drying an aliquot of the reaction mixture, weighing the polymeric residue and calculating the percent solids. The amount of water needed for the dilution was then calculated. 74.2 kg of Triton® X-200 was charged to the batch and mixed for thirty minutes after which the batch was drained through an 80 mesh screen filter to provide a 25% solids batch of the desired copolymer.

EXAMPLE 7

Preparation of Adhesive Blend Coated on a Release Liner

A Blended Adhesive of Example 5 was coated from a hopper knife coater of suitable size onto a 50 yard (45.7 m) length of a 4 mil (1.02 mm) thick and 20 in (50.8 cm) wide, silicone-coated release liner (available from Release International, Iowa City, Iowa as 211A 72# Stick-Not Grade 8527) at a coating weight of 12 grains per 4×6 inch sample (50 grams per square meter) and dried by heating in an oven at temperatures of 110° F. (43° C.) for Zone 1, 165° F. (74° C.) for Zone 2 and 225° F. (107° C.) for Zone 3 at a line speed of about 16.5 feet per minute ($5.03^m/_{min}$).

TABLE 1

| Sample | Porous Backing | Migration Barrier | Adhesive | Silicone-Coated Release Liner |
|---|---|---|---|---|
| Ex. 8 | None | Ethyl acrylate/tertiary butylacrylamide copolymer (hereinafter EA/t as prepared in Ex. 6) | Adhesive Blend (prepared in Ex. 5) | Yes |
| Ex. 9 | Meltdown Polyurethane | EA/t (Ex. 6) | Adhesive Blend (Ex. 5) | Yes |
| Ex. 10 | None | None | Hydrophilic Adhesive (prepared in Ex. 4) | Yes |
| Ex. 11 | None | EA/t (Ex. 6) | Hydrophilic Adhesive (Ex. 4) | Yes |
| Ex. 12 | None | Polyurethane Barrier | Hydrophilic Adhesive (Ex. 4) | Yes |
| Ex. 13 | Meltblown Polyurethane (Ex. 9) | Polyurethane Barrier (Ex. 12) | Hydrophilic Adhesive (Ex. 4) | Yes |
| Ex. 14 | None | MRP Adhesive (described in Ex. 2) | Hydrophilic Adhesive (Ex. 4) | Yes |
| Ex. 15 | None | EA/t (Ex. 6) with MRP Adhesive (Ex. 2) coated thereon | Hydrophiic Adhesive (Ex. 4) | Yes |
| Control Ex. 16 | Meltblown Polyurethane | None | Hydrophilic Adhesive (Ex. 4) | Yes |
| Ex. 17 | Meltblown Polyurethane (Ex. 9) Pressure Laminated | EA/t (Ex. 6) | Hydrophilic Adhesive (Ex. 4) | Yes |
| Ex. 18 | Meltblown Polyurethane (Ex. 9) | MRP Adhesive (Ex. 2) | Hydrophilic Adhesive (Ex. 4) | Yes |
| Ex. 19 | Meltblown Polyurethane (Ex. 9) | EA/t (Ex. 6) with MRP Adhesive (Ex. 2) coated thereon | Hydrophilic Adhesive (Ex. 4) | Yes |

EXAMPLE 8

Coating Migration Barrier Layer onto Adhesive Blend

The dried adhesive copolymer blend on release liner from Example 7 was flood coated with a 33% solids batch of the ethyl acrylate-N-tertiary butylacrylamide copolymer made as described in Example 6 using a Meier bar apparatus at a line speed of about 20 yards per minute at a coating weight of 2 grains per 4×6 inch sample (8 g/m$^2$). The article obtained was dried at an oven temperature of 225° F. (107° C).

EXAMPLE 9

Preparation of an Article of the Invention Using Blend Adhesive and Polyurethane Non-Woven Backing The barrier layer/adhesive blend/release liner composite from Example 8 was used to collect a non-woven polyurethane backing layer.

The polyurethane was melt blown using a process similar to the process reported in Wente, Van A., "Superfine Thermoplastic Fibers" in *Industrial Engineering Chemistry*, Vol. 48, pages 1342 et seq (1965), or in Report No. 4364 of the Naval Research Laboratories, published May 25, 1954 titled "Manufacture of Superfine Organic Fibers", by Wente, Van A., Boone, C. D. and Fluharty, E. L. (which is herein incorporated by reference) except that the melt blowing die had smooth surface orifices (10/cm) with an 8:1 length to diameter ratio. The die temperature was maintained at 226° C., the primary air temperature and pressure were 235° C. and 150 kPa, respectively (0.76 mm gap width), and the polymer throughput rate was 131 gm/hr/cm. The resulting webs had an average fiber diameter of about 10–15 microns, basis weight of 102 g/m$^2$ and thickness of about 13 mils (0.33 min) and were extruded at about 14 pounds per hour (6.36 kg per hour) directly onto the adhesive layer on a heated (88 to 93° C.) collector positioned 6 inches (15.2 cm) from the die to provide a backing. The polyurethane used for the backing was Morton PUR 440-200 (available from Morton International Inc., Chicago, Ill.) with 4 percent tan pigment (color number 1093538 available from Reed Spectrum, a division of Sandoz Chemicals Corp., Minneapolis, Minn.). The tape was allowed to cool under ambient conditions.

The tape was gamma irradiated using conventional production equipment to a total dose of about 30–35 Kilograys. The tape was tested for MVTR and the results are provided in Table 2.

EXAMPLE 10

Preparation of a Liner Coated with Hydrophilic Pressure-Sensitive Adhesive

A 50% solids hydrophilic adhesive from Example 4 was knife coated from solution onto a 4 mil (1 mm) thick and 9 in (23 cm) wide silicone-coated liner (as used in Example 7) at about 11 grains per 4 by 6 inch section (46 g/m$^2$) at a knife coater gap of about 5 mil (12.6 mm). The adhesive layer was dried as described in Example 7.

EXAMPLE 11

Preparation of Migration Barrier Coated Hydrophilic Adhesive

The adhesive coated on release liner from Example 10 was flood coated with a coating of about 2 grains per 4×6 inch section (8 g/m$^2$) of the copolymer of ethyl acrylate/N-tertiary butylacrylamide prepared as described in Example 6 using a Meier bar coater from solution. The article was oven dried.

Figure 3:
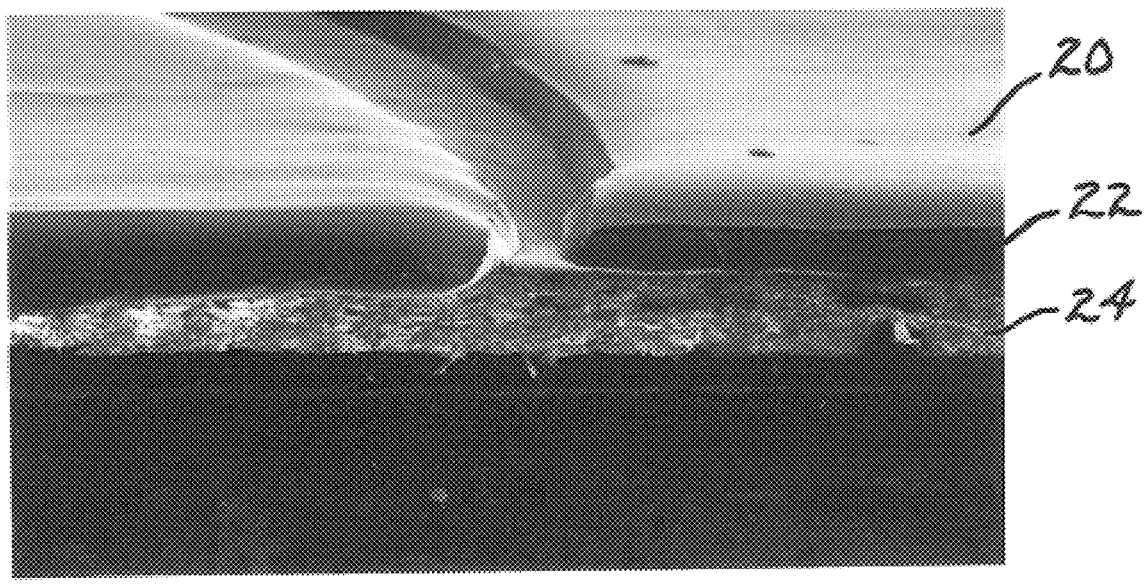
FIG. 3 is a 100 times magnification SEM of a migration barrier/adhesive/release liner composite.
Figure 4:
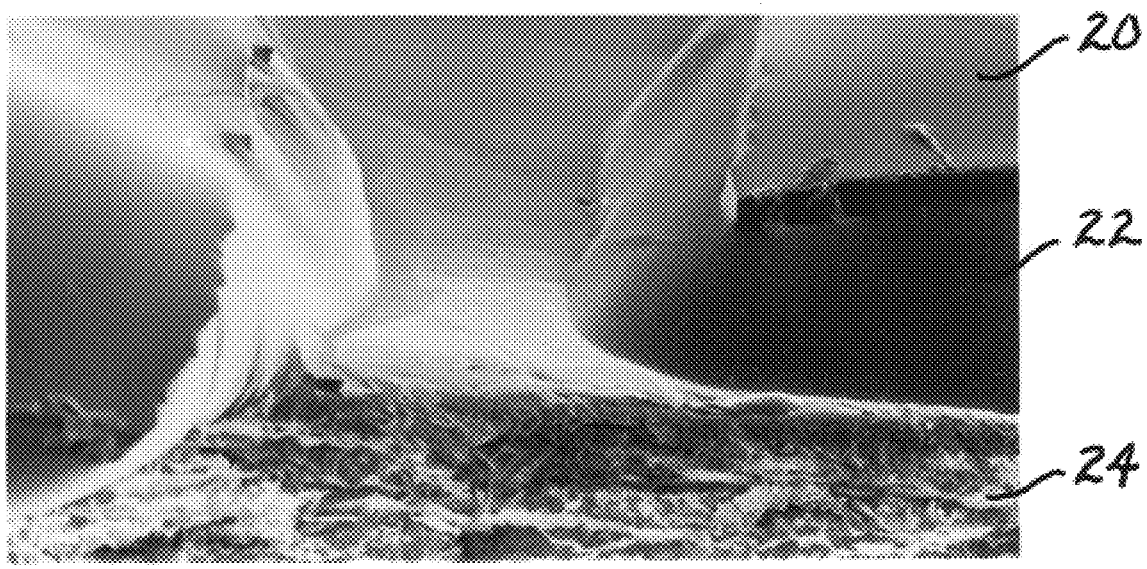
FIG. 4 is a 500 times magnification of the composite shown in FIG. 3.

FIGS. 3 and 4 are scanning electron micrographs of a sample prepared according to Example 11. FIG. 3 is a 100 times magnification and FIG. 4 is a 500 times magnification of the sample. Although it is not essential to the present invention that the migration barrier and the adhesive layer remain as disinct layers, FIGS. 3 and 4 illustrate that the migration barrier 20 is apparent as a distinct layer apart from the adhesive layer 22. The silicone coated release liner is depicted as 24 in both FIGS. 3 and 4.

EXAMPLE 12

Preparation of a Polyurethane Migration Barrier Layer Coated on Hydrophilic Adhesive A batch of an aqueous (62% solids) dispersion of a polyurethane polymer, Witcobond-290H diluted to 31% solids (available from Witco Corp., Greenwich, Conn.) was flood coated using a method similar to the method described in Example 8. That is, it was coated by pouring the polyurethane dispersion over the adhesive side of the adhesive coated release liner article of Example 10 and the polyurethane was then spread with a 0.5 inch (1.27 cm) diameter cylindrical rod to a coating weight of 2 grains per 4×6 inch section (8g/m$^2$). The article was dried at 225° F. (107° C.) in an oven for 10 minutes.

EXAMPLE 13

Preparation of a Tape Article of the Invention

The article of Example 12 was coated as described in Example 9 with the same melt blown polyurethane backing and the collector drum used was heated at 180 to 190° F. (82 to 88° C.). The pressure-sensitive adhesive tape article was gamma irradiated to a total dose of 30 to 40 kilograys and tested for moisture vapor transmission. Moisture vapor transmission results are provided in Table 2.

EXAMPLE 14

Preparation of a Migration Barrier Layer-Adhesive Article

A hydrophilic adhesive/silicone release liner composite prepared as described in Example 10 was coated with a barrier layer comprising the copolymer of Example 2 using a knife coater with a coating gap of 2 mils (0.051 mm). The wet coating was dried at room temperature for 10 minutes, then in an oven at 225° F. (107° C.) for 25 minutes to achieve a dry coating weight of 6 grains per 4 by 6 inch section (24 g/m$^2$).

EXAMPLE 15

Preparation of Multiple Layer Adhesive Article

A 36 inch length (0.91 m)×6 inch width (15.2 cm) of the migration barrier/hydrophilic adhesive/liner composite described in Example 11 was coated with a dispersion of the copolymer (MRP Adhesive) described in Example 2 using a knife coater with a gap of 2 mils (0.051 mm). The resulting article was dried at room temperature (about 25° C.) for 10 minutes and then dried in an oven at 225° F. (107° C.) for 25 minutes to obtain a dry coating weight of 6 grains per 4 by 6 inch section (24 g/m$^2$).

Comparative Example 16

Preparation of a Control Tape Article

A polyurethane non-woven web was melt blown using the method described in Example 9 to provide a nonwoven web with a basis weight of 120 g/m, a thickness of 15.8 mil (0.40 mm) and an average fiber diameter of about 10–15 microns. The nonwoven web was then pressure laminated onto the hydrophilic adhesive on silicone-coated liner prepared as described in Example 10. The lamination was accomplished at room temperature and at a pressure of 20 psi with a line speed of 3 feet (0.91 m) per minute. A portion of this sample was gamma irradiated at 30 to 35 kGy total dose to crosslink the adhesive. The irradiated portion of the sample was tested for MVTR and the results are provided in Table 2.

FIG. 1 is a scanning electron micrograph of the sample prepared according to Example 16. The sample shown in FIG. 1 was held for 14 days at 120° F. at 90% relative humidity. These are the parameters at which samples are generally held to accelerate the aging process. Eleven days at 120° F. (49° C.) and 90% relative humidity is considered a good approximation of one year aging under ambient conditions. Since the sample in FIG. 1 lacks the migration barrier, the adhesive 14 freely migrates into the interstices of the nonwoven web 16 and settles between the individual fibers 18 which comprise the nonwoven web 16.

EXAMPLE 17

Preparation of a Tape Article of the Invention

The article of Example 11 (migration barrier of ethyl acrylate/N-tertiary butylacrylamide copolymer/Hydrophilic Adhesive/liner composite) was coated with the same melt blown polyurethane backing as described in Example 9. The backing had a basis weight of 122 g/m, web thickness of 15.7 mil (0.40 mm) and effective fiber diameter of 17.8 microns. The collector drum was heated to about 190 to 200° F. (88 to 93° C.). The pressure-sensitive adhesive tape article was gamma irradiated to a total dose of 30 to 35 kGy and tested for moisture vapor transmission. The resulting article had an acceptable moisture vapor transmission rate and results are given in Table 2.

EXAMPLE 18

Preparation of a Porous Backing Tape Article of the Invention

The article of Example 14 (migration barrier of the isooctyl acrylate-acrylic acid-macromer copolymer of Example 2 coated on the hydrophilic adhesive of Example 4 on a silicone-coated liner) was coated as described in Example 9 with the same melt blown polyurethane backing at the same basis weight, web thickness and effective fiber diameter but the collector drum was not heated. The resultant composite was dried in an oven as detailed in Example 7. The dried article was gamma irradiated to a total dose of 30 to 35 kilograys. The article was tested for MVTR and the results are shown in Table 2.

Figure 2:
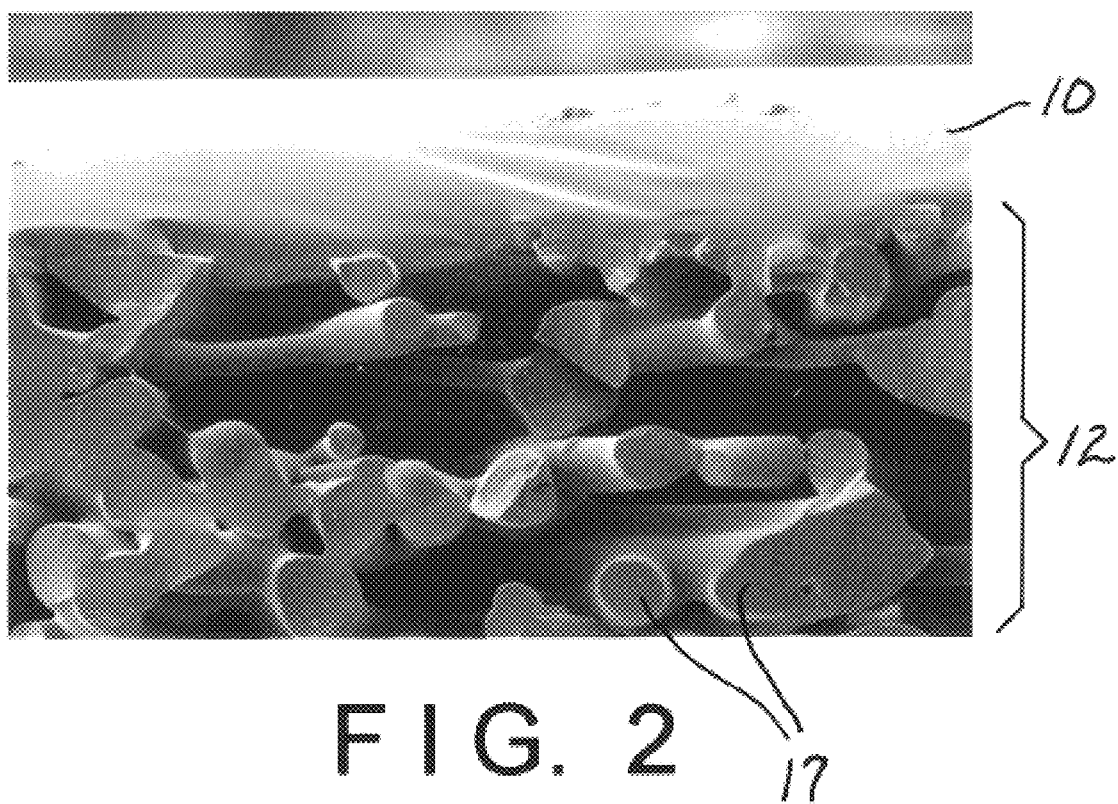
FIG. 2 is a 500 times magnification SEM of an embodiment of the invention.
Figure 5:
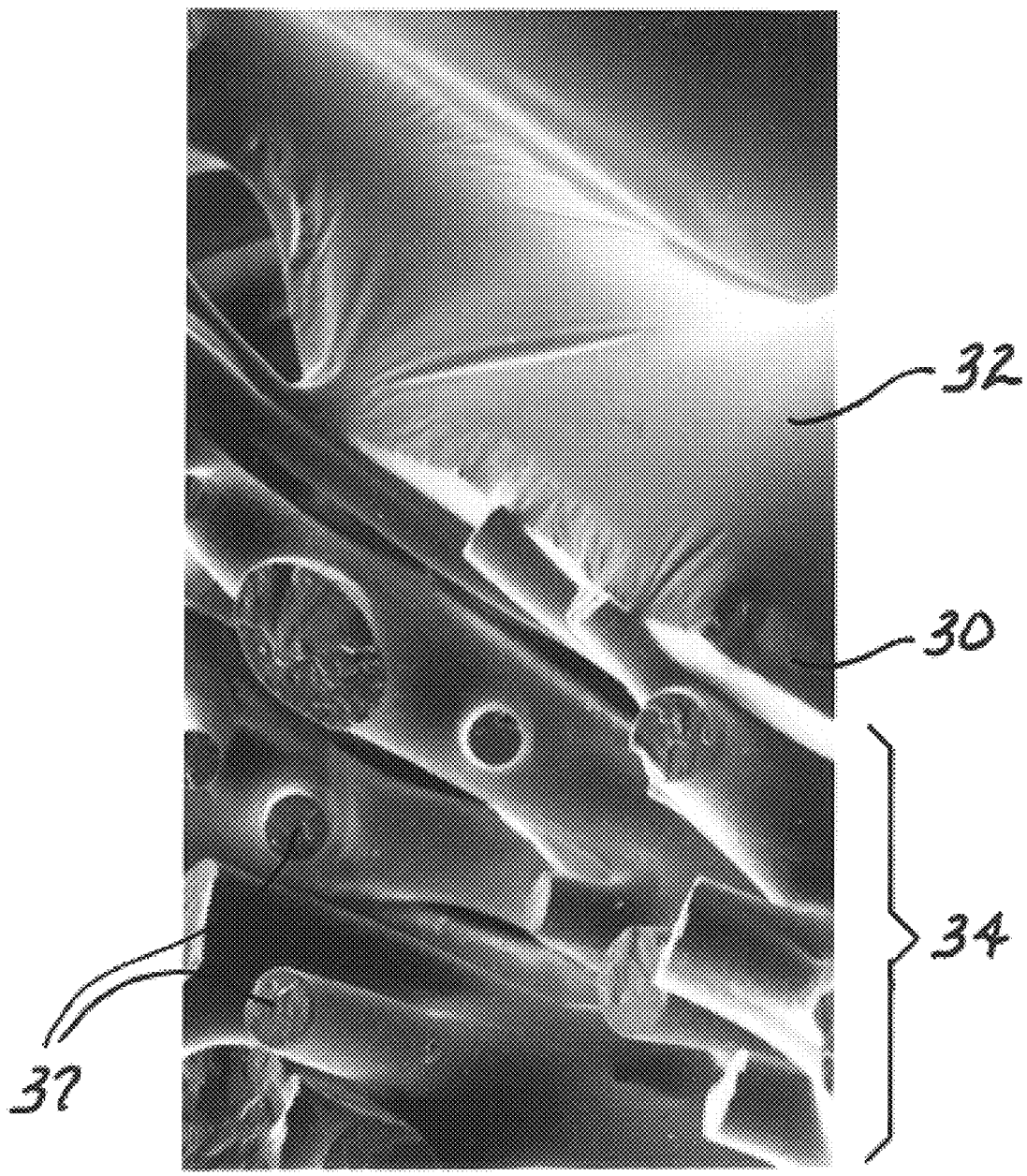
FIG. 5 is a 900 times magnification of the sample shown in FIG. 2.

FIGS. 2 and 5 are scanning electron micrographs of the sample prepared according to Example 17 and held for 14 days at 120° F. and 90% relative humidity (accelerated aging described above in Example 16). At the 500 times magnification used for FIG. 2, the migration barrier is not evident as a distinct layer apart from the adhesive layer. However, FIG. 2 shows that the adhesive (10) does not migrate into the interstices of the nonwoven backing 12 comprised of fibers 17. FIG. 5 (900× magnification) more clearly shows the migration barrier 30 as a distinct layer apart from the adhesive 32. FIG. 5 also shows that the adhesive 32 does not flow into the interstices of the nonwoven web 34 comprised of fibers 37. The migration barrier 30 shown best in FIG. 5 is about 6–7 μm thick.

EXAMPLE 19

Preparation of a Tape Article

The article of Example 15 (first layer of silicone-coated liner, second layer of hydrophilic adhesive, third layer of ethyl acrylate/N-tertiary butylacrylamide copolymer migration barrier and fourth layer of isooctyl acrylate-acrylic acid-macromer copolymer) was used to collect a melt blown polyurethane backing prepared as described in Example 9 at the same basis weight, web thickness and fiber diameter but the collector drum was not heated. The finished article was gamma irradiated to a total dose of 30 to 35 kilograys. The resultant article was tested for MVTR and the results are provided in Table 2.

EXAMPLE 20

The moisture vapor transmission rate of the tape articles described in Examples 9, 13, 16, 17, 18 and 19 above was measured using the test method described above.

The results are shown in Table 2.

TABLE 2

| ARTICLE OF EXAMPLE NO. | MVTR (g/m²/24 hours) |
| --- | --- |
| Example 16 (Control) | 712.8 |
| Example 9 | 689.9 |
| Example 13 | 809.6 |
| Example 17 | 933.6 |
| Example 18 | 581.1 |
| Example 19 | 594.1 |

The conclusion derived from this data is that MVTR is not substantially reduced by the presence of a barrier layer.

The migration barriers were examined by scanning electron microscope. For examples 9, 13, 17, 18 and 19 a barrier was detected, preventing the migration of adhesive into the interstices of the porous backing.

What is claimed is:

1. A first aid dressing comprised of at least three layers, said three layers comprised of a porous backing, a migration barrier layer and adhesive wherein said migration barrier layer is juxtaposed between said porous backing and said adhesive; wherein said first aid dressing has a moisture vapor transmission rate of at least 400 g/m² per 24 hours and does not include an additional adhesive between said migration barrier and said porous backing and further wherein an absorbent layer is adhered to at least a portion of said adhesive layer.

2. A first aid dressing comprised of:

at least three layers, said three layers comprised of a porous backing, a migration barrier layer and adhesive, wherein said migration barrier layer is juxtaposed between said porous backing and said adhesive and is 20 micrometers thick or less; and an absorbent layer adhered to at least a portion of said adhesive, wherein said dressing does not include an additional adhesive between said migration barrier layer and said porous backing.

3. The first aid dressing of claim 1 or 2 wherein said absorbent layer is selected from the group consisting of a woven material and a nonwoven material.

4. The first aid dressing of claim 3 wherein said absorbent material is selected from the group consisting of rayon, polyester, polyurethane, polyolefin, cellulose, cellulose derivatives, cotton, orlon, nylon and hydrogel polymeric material.

5. The first aid dressing of claim 4 wherein said absorbent layer is comprised of a nonwoven rayon web.

6. The first aid dressing of claim 4 wherein said migration barrier substantially prevents said adhesive from migrating into said porous backing.

7. An adhesive sheet article comprising:

a porous backing;

an adhesive; and a migration barrier comprising a polymeric coating selected from the group of an alkyl acrylate-N-alkylacrylamide copolymer, polyurethane, and mixtures thereof, wherein said migration barrier has a thickness of about 20 micrometers or less and is juxtaposed between said backing and said adhesive without an additional adhesive between said migration barrier and said porous backing so that said migration barrier substantially prevents said adhesive from migrating into said backing; wherein said adhesive sheet article has a moisture vapor transmission rate of about 400 g/m$^2$ per 24 hours or more.

8. A dressing article comprising the adhesive sheet article of claim 7 and an absorbent layer, wherein a first surface of said absorbent layer is adhered to said adhesive opposed to said backing.

9. The adhesive sheet article of claim 7, wherein the porous backing is selected from the group consisting of a woven fabric, a non-woven fabric, and a knitted fabric.

10. The adhesive sheet article of claim 9 wherein said porous backing is a non-woven web.

11. The dressing article of claim 8 wherein said absorbent layer is selected from the group consisting of rayon, polyester, polyurethane, polyolefin, cellulose, cellulose derivatives, cotton, rayon, orlon, nylon, and hydrogel polymeric material.

12. The dressing article of claim 11 wherein said absorbent layer is comprised of a nonwoven rayon web.

* * * * *

UNITED STATES PATENT AND TRADEMARK OFFICE
CERTIFICATE OF CORRECTION

PATENT NO.    : 5,914,282
DATED         : June 22, 1999
INVENTOR(S)   : Dunshee, Wayne K.

It is certified that error appears in the above-identified patent and that said Letters Patent is hereby corrected as shown below:

<u>Column 3,</u>
Lines 32-33, delete the words "copending application F.N. 51439USA4A" and insert in place thereof -- U.S. Pat. No. 5,648,166 --.

<u>Column 6,</u>
Line 45, delete the term "a,a'-azobisisobutyronitrile" and insert in place thereof -- 2,2'-azobisisobutyronitrile --

Signed and Sealed this

Twenty-third Day of April, 2002

Attest:

JAMES E. ROGAN
*Director of the United States Patent and Trademark Office*

*Attesting Officer*